United States Patent
Higashimura et al.

(10) Patent No.: US 7,161,000 B2
(45) Date of Patent: Jan. 9, 2007

(54) METHOD FOR PRODUCING PHENOL CONDENSATE

(75) Inventors: Hideyuki Higashimura, Tsukuba (JP); Eiichi Kotake, Tsukuba (JP); Masaaki Kubota, Tsukuba (JP); Shiro Kobayashi, Kyoto (JP)

(73) Assignee: Sumitomo Chemical Company, Limited, Osaka (JP)

( * ) Notice: Subject to any disclaimer, the term of this patent is extended or adjusted under 35 U.S.C. 154(b) by 392 days.

(21) Appl. No.: 10/854,334

(22) Filed: May 27, 2004

(65) Prior Publication Data

US 2004/0267057 A1    Dec. 30, 2004

(30) Foreign Application Priority Data

May 30, 2003  (JP)  ............................. 2003-154748
May 30, 2003  (JP)  ............................. 2003-154749

(51) Int. Cl.
*C07D 225/00* (2006.01)
*C07C 39/12* (2006.01)

(52) U.S. Cl. ...................... 540/465; 540/450; 540/470; 540/484; 540/541; 568/717

(58) Field of Classification Search ................ 540/450, 540/465, 470, 484, 541; 568/717
See application file for complete search history.

(56) References Cited

U.S. PATENT DOCUMENTS 5,247,075 A * 9/1993 Parker et al. ............... 540/465
5,284,944 A * 2/1994 Madison et al. ............ 540/474

FOREIGN PATENT DOCUMENTS

JP    2002-35592 A  *  5/2002

OTHER PUBLICATIONS

Hideyuki Higashimura et al.; "Radical-Controlled" Oxidative Polymerization of 4-Phenoxyphenol by a Tyrosinase Model Complex Catalyst to Poly(1,4-phenylene oxide); Macromolecules 2000, vol. 33, pp. 1986-1995.

* cited by examiner

*Primary Examiner*—Porfirio Nazario-Gonzalez
(74) *Attorney, Agent, or Firm*—Birch, Stewart, Kolasch & Birch, LLP

(57) ABSTRACT

Provided is a method for producing a phenol condensate by oxidative condensation of a phenol compound not having a substituted group on at least one ortho-position, in the presence of a specific complex (II) and oxygen, wherein a condensate coupled at para-position of the phenol can be produced in an excellent yield, $$L\text{-}M(X)_n \quad (II)$$

wherein L represents a ligand having 2 to 4 nitrogen atoms as donor atoms, M represents copper ion, nickel ion, cobalt ion, iron ion, manganese ion, chromium ion or vanadyl ion, X represents a counter ion, n is a number of Xs.

5 Claims, No Drawings

METHOD FOR PRODUCING PHENOL CONDENSATE

This Nonprovisional application claims priority under 35 U.S.C. § 119(a) on Patent Application No(s). 2003-154748 and 2003-154749 filed in JAPAN on May 30, 2003, the entire contents of which are hereby incorporated by reference.

BACKGROUND OF THE INVENTION

1. Field of the Invention

The present invention relates to a method for producing a phenol condensate.

2. Description of the Related Art

A phenol condensate is a dehydrogenated condensate which is produced formally by removing hydrogen atom from phenol compound and the dehydrogenated species are connected with one another. As a method for producing thereof, it has been known that a phenol compound is subjected to oxidative condensation in the presence of catalyst and oxygen.

For example, it is known that, when 2,6-disubstituted phenol compound is subjected to oxidative condensation in the presence of copper complex and oxygen, poly(2,6-disubstituted-1,4-phenyleneoxide) is obtained by coupling of a para-positioned carbon atom with oxygen atom.

On the other hand, when a phenol condensate is produced by subjecting a phenol compound not having a substituted group on at least one ortho-position to oxidative condensation, there has been a problem that condensates coupled not only at the para-positioned carbon but also at the ortho-positioned carbon are formed.

The present inventors have reported a method for producing phenol condensate (Macromolecules 33, 1986 (2000)) that 4-phenoxyphenol, which is a phenol compound not having a substituted group on at least one ortho-position, is subjected to oxidative condensation in the presence of a copper complex represented by the following formula and of oxygen,

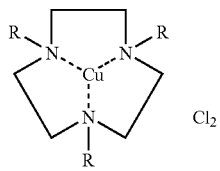

wherein R is n-butyl group, isopropyl group or cyclohexyl group; however the yield of condensate coupled at the para-position is not yet sufficient.

SUMMARY OF THE INVENTION

The object of the present invention is to provide a method for producing phenol condensate by subjecting a phenol compound not having a substituent on at least one ortho-position to oxidative condensation, and for producing a condensate coupled at para-position in an excellent yield.

After having intensively studied to achieve the above purpose, the present inventors have found that, when phenol condensate is produced by a method using a specific complex, the yield of condensate coupled at para-position is excellent; thus have completed the present invention.

That is, the present invention provide a method for producing phenol condensate comprising oxidative condensation of a phenol compound represented by the following formula (I), in the presence of a complex represented by the following formula (II), and oxygen,

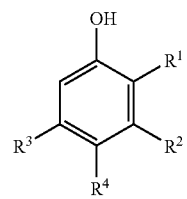

wherein $R^1$, $R^2$ and $R^3$ independently represent hydrogen atom, hydrocarbon group, substituted hydrocarbon group, hydrocarbonoxy group, substituted hydrocarbonoxy group or halogen atoms, $R^1$ and $R^2$ may together form a ring and $R^4$ represents hydrogen atom or phenoxy group, $$L\text{-}M\,(X)_n \quad (II)$$

wherein L represents a ligand having 2 to 4 nitrogen atoms as donor atoms, M represents copper ion, nickel ion, cobalt ion, iron ion, manganese ion, chromium ion or vanadyl ion, X represents a counter ion, n is a number of Xs and is fixed depending on the valences of L, M and X;

active parameter Eact. (kcal/mol) defined by the following formula (A) is −21.1 or less and selective parameter Eselect. (kcal/mol) defined by the following formula (B) is −1.7 or less, $$Eact.=E(a)-E(c)-E(d) \quad (A)$$

$$Eselect.=\{E(a)-E(d)\}-\{E(b)-E(e)\} \quad (B)$$

wherein E(a) to E(e) represent a heat of formation (kcal/mol) when the following structural formulas of from (a) to (e) are respectively structurally optimized with semiempirical molecular orbital method AM1;

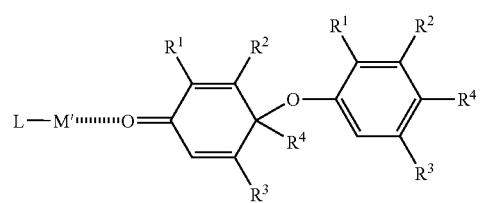

(a)

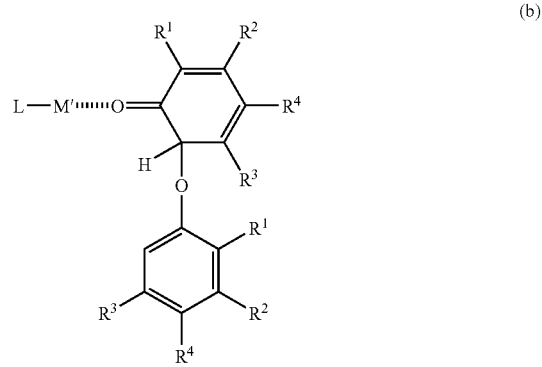

(b)

-continued

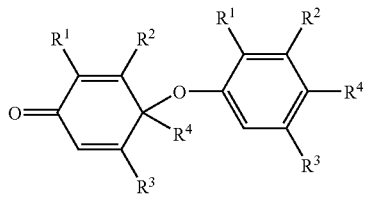
(c)
(d)

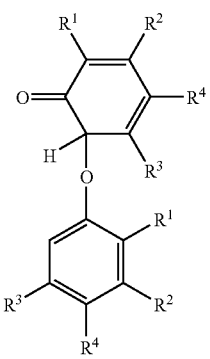
(e)

wherein $R^1$, $R^2$, $R^3$ and $R^4$ represent the same meaning represented in the above formula (I), L, X and n represent the same meaning represented in the above formula (II), and M' respectively represents monovalent copper ion when M is copper ion, divalent nickel ion when M is nickel ion, divalent cobalt ion when M is cobalt ion, divalent iron ion when M is iron ion, divalent manganese ion when M is manganese ion, divalent chromium ion when M is chromium ion or divalent vanadyl ion when M is vanadyl ion.

DETAILED DESCRIPTION OF THE INVENTION $R^1$, $R^2$ and $R^3$ in formula (I) independently represent hydrogen atom, hydrocarbon group, substituted hydrocarbon group, hydrocarbonoxy group, substituted hydrocarbonoxy group or halogen atoms, and $R^3$ and $R^2$ may together form a ring.

$R^1$, $R^2$ and $R^3$ in formula (I) include non-cyclic saturated hydrocarbon groups having 1 to about 50 carbon atoms, such as methyl group, ethyl group, propyl group, isopropyl group, butyl group, isobutyl group, t-butyl group, pentyl group, hexyl group, nonyl group, dodecyl group, pentadecyl group, octadecyl group, dococyl group and the like; saturated hydrocarbon groups with cyclic structures having 3 to about 50 carbon atoms, such as cyclopropyl group, cyclobutyl group, cyclobutyl group, cyclopentyl group, cyclohexyl group, cyclononyl group, cyclododecyl group, norbornyl group, adamanthyl group, cyclohexylmethyl group and the like; alkenyl groups having 2 to about 50 carbon atoms such as ethenyl group, propen-1-yl group, propen-2-yl group, propen-3-yl group, 3-buten-1-yl group, 2-buten-1-yl group, 2-penten-1-yl group, 2-hexen-1-yl group, 2-nonen-1-yl group, 2-dodecen-1-yl group, and the like; alkynyl groups having 2 to about 50 carbon atom such as ethynyl group, propyn-1-yl group, propyn-2-yl group, 3-butyn-1-yl group, 2-butyn-1-yl group, 2-pentyn-1-yl group, 2-hexyn-1-yl group, 2-nonyn-1-yl group, 2-dodecyn-1-yl group, and the like; aryl groups having 6 to about 50 carbon atoms such as phenyl group, 1-naphthyl group, 2-naphthyl group, 2-methylphenyl group, 3-methylphenyl group, 4-methylphenyl group, 4-ethylphenyl group, 4-propylphenyl group, 4-isopropylphenyl group, 4-butylphenyl group, 4-t-butylphenyl group, 4-hexylphenyl group, 4-cyclohexylphenyl group, 4-adamanthylphenyl group, 4-phenylphenyl group and the like; aralkyl groups having 7 to about 50 carbon atoms such as phenylmethyl group, 1-phenylethyl group, 2-phenylethyl group, 1-phenyl-1-propyl group, 1-phenyl-2-propyl group, 2-phenyl-2-propyl group, 1-phenyl-3-propyl group, 1-phenyl-4-butyl group, 1-phenyl-5-pentyl group, 1-phenyl-6-hexyl group and the like. Said hydrocarbon group is preferably hydrocarbon groups having 1 to 30 carbon atoms, more preferably hydrocarbon groups having 1 to 16 carbon atoms and further more preferably hydrocarbon groups having 1 to 6 carbon atoms.

Substituted hydrocarbon group of $R^1$, $R^2$ and $R^3$ in the above formula (I) includes the above hydrocarbon groups substituted with halogen atoms, hydroxy group, alkoxy group, amino group, substituted amino group, nitro group, trialkylsilyl group and the like. Said subsutituted hydrocarbon group is preferably subsutituted hydrocarbon groups having 1 to 40 carbon atoms, more preferably subsutituted hydrocarbon groups having 1 to 20 carbon atoms and further more preferably subsutituted hydrocarbon groups having 1 to 8 carbon atoms.

Hydrocarbonoxy group of $R^1$, $R^2$ and $R^3$ in the above formula (I) include non-cyclic saturated hydrocarbonoxy groups having 1 to about 50 carbon atoms such as methyloxy group, ethyloxy group, propyloxy group, isopropyloxy group, butyloxy group, isobutyloxy group, t-butyloxy group, pentyloxy group, hexyloxy group, nonyloxy group, dodecyloxy group, pentadecyloxy group, octadecyloxy group, dococyloxy group and the like; saturated hydrocarbonoxy groups with cyclic structure having 3 to about 50 carbon atoms such as cyclopropyloxy group, cyclobutyloxy group, cyclobutyloxy group, cyclopentyloxy group, cyclohexyloxy group, cyclononyloxy group, cyclododecyloxy group, cyclonorbornyloxy group, adamanthyloxy group, cyclohexylmethyloxy group and the like; alkenyloxy groups having 2 to about 50 carbon atoms such as propen-1-yloxy group, propen-2-yloxy group, propen-3-yloxy group, 3-buten-1-yloxy group, 2-buten-1-yloxy group, 2-penten-1-yloxygroup, 2-hexen-1-yloxygroup, 2-nonen-1-yloxy group, 2-dodecen-1-yloxy group, and the like; alkynyloxy groups having 2 to about 50 carbon atoms such as ethynyl group, propyn-2-yloxy group, butyn-2-yloxy group, pentyn-2-yloxy group, hexyn-2-yloxy group, nonyn-2-yloxy group, dodecyn-2-yloxy group, and the like; aryloxy groups having 6 to about 50 carbon atoms such as phenoxy group, 1-naphthyloxy group, 2-naphthyloxy group, 2-methylphenyloxy group, 3-methylphenyloxy group, 4-methylphenyloxy group, 4-ethylphenyloxy group, 4-propylphenyloxy group, 4-isopropylphenyloxy group, 4-butylphenyloxy group, 4-t-butylphenyloxy group, 4-hexylphenyloxy group, 4-cyclohexylphenyloxy group, 4-adamanthylphenyloxy group, 4-phenylphenyloxy group and the like; aralkyloxy groups having 7 to about 50 carbon atoms such as phenylmethyloxy group, 1-phenylethyloxy group, 2-phenylethyloxy group, 1-phenyl-1-propyloxy group, 1-phenyl-2-propyloxy group, 2-phenyl-2-propyloxy group, 1-phenyl-3-propyloxy group, 1-phenyl-4-butyloxy group, 1-phenyl-5-pentyloxy group, 1-phenyl-6-hexyloxy group and the like. Said hydrocarbonoxy group is preferably hydrocarbonoxy groups having 1 to 30 carbon atoms, more preferably hydrocarbonoxy groups having 1 to 16 carbon atoms and further more preferably hydrocarbonoxy groups having 1 to 6 carbon atoms.

Substituted hydrocarbonoxy group of $R^1$, $R^2$ and $R^3$ in the above formula (I) includes above described hydrocarbonoxy groups substituted with halogen atoms, hydroxy group, alkoxy group, amino group, substituted amino group, nitro group, trialkylsilyl group and the like. Said subsutituted hydrocarbonoxy group is preferably subsutituted hydrocarbonoxy groups having 1 to 40 carbon atoms, more preferably subsutituted hydrocarbonoxy groups having 1 to 20 carbon atoms and further more preferably subsutituted hydrocarbonoxy groups having 1 to 8 carbon atoms.

Halogen atoms of $R^1$, $R^2$ and $R^3$ in the above formula (I) includes fluorine atom, chlorine atom, bromine atom or iodine atom. Said halogen atoms is preferably fluorine atom, chlorine atom or bromine atom, more preferably fluorine atom or chlorine atom, further more preferably fluorine atom.

The case that $R^1$ and $R^2$ in the above formula (I) are connected to form a ring includes, for example, —$CH_2$ $CH_2$ $CH_2$— group, —$CH_2$ $CH_2$ $CH_2$ $CH_2$— group and —CH=CH—CH=CH— group.

$R^1$, $R^2$ and $R^3$ in the above formula (I) are preferably hydrogen atom, hydrocarbon group, hydrocarbonoxy group or halogen atoms, more preferably hydrogen atom or hydrocarbon group, further more preferably hydrogen atom or hydrocarbon group having 1 to 4 carbon atoms, particularly preferably hydrogen atom or methyl group.

$R^4$ in the above formula (I) represents hydrogen atom or phenoxy group.

Typical examples of phenol compound include phenol, 2-methylphenol, 3-methylphenol, 2,3-dimethylphenol, 2,5-dimethylphenol, 2,3,5-trimethylphenol, 2-ethylphenol, 2-propylphenol, 2-isopropylphenol, 2-bytylphenol, 2-isobytylphenol, 2-t-bytylphenol, 2-pentylphenol, 2-hexylphenol, 2-nonylphenol, 2-dodecylphenol, 2-pentadecylphenol, 2-octadecylphenol, 2-dococylphenol, 2-cyclopentylphenol, 2-cyclohexylphenol, 2-adamanthylphenol, 2-ethenylphenol, 2-propyn-1-ylphenol, 2-penpyn-2-ylphenol, 2-penpyn-3-ylphenol, 2-ethynylphenol, 2-phenylphenol, 2-(1-naphthyl)phenol, 2-(2-naphthyl)phenol, 2-(4-t-butylphenyl)phenol, 2-(4-cyclohexylphenyl)phenol, 2-(4-adamanthylphenyl) phenol, 2-(4-phenylphenyl)phenol, 2-(phenylmethyl)phenol, 2-(2-phenylethyl)phenol, 2-(trimethylsilylethenyl)phenol, 2-methoxyphenol, 2-phenoxyphenol, 4-phenoxyphenol, 2-fluorophenol and the like.

Of the method for producing phenol condensate of the present invention, as a starting raw material, above mentioned phenol compounds may be used alone or in the mixture thereof.

A complex used is represented by the following formula (II),

L-M (X)$_n$          (II)

wherein L represents a ligand having 2 to 4 nitrogen atoms as donor atoms, M represents copper ion, nickel ion, cobalt ion, iron ion, manganese ion, chromium ion or vanadyl ion, X represents a counter ion, n is a number of Xs and is fixed depending on the valences of L, M and X;

active parameter Eact. (kcal/mol) defined by the above formula (A) is −21.1 or less and selective parameter Eselect. (kcal/mol) defined by the above formula (B) is −1.7 or less.

L is not particularly limited provided that L is a ligand of which donor atoms are 2 to 4 nitrogen atoms; but the number of said atoms is preferably 2 to 4, more preferably 3.

The ligand of the present invention defines molecules or ions coordination-bonding to an atom as described in KAGAKUDAIJITEN(the first version, TOKYO KAGAKU DOZIN CO., 1989). The atom directly links to coordination-bonding is called a donor atom.

The ligands having two donor atoms are illustrated in JP-A-2001-302788. Specifically, they are ethylenediamine, 1,3-propanediamine, 1,2-cyclohexanediamine, 1,2-phenylenediamine, 2,2'-bipyridyl, 2,3-butanedioxime, 2,4-pentanedioxime, 2,3-bis(N-methylimino)-butane, 2,3-bis(N-phenylimino)-butane, 1,3-bis(N-methylimino)-butane, 2,4-bis(N-methylimino)-pentane and the like, and derivatives thereof.

The ligands having four donor atoms are illustrated in JP-A-H9-324042. Specifically, they are tris(2-pyridylmethyl)amine, tris(2-imidazolylmethyl)amine, tris(2-benzoxazolylmethyl)amine, tris(2-benzthiazolylmethyl)amine, tris(1-pyrazolylmethyl)amine, tris(2-pyridyl-2-ethyl)amine, triethylenetetramine, N,N'-bis(2-pyridylmethyl)ethylenediamine, N,N'-bis(2-amino-3-benzylidene)ethylenediamine, 1,4,8,11-tetraazacyclotetradecane, porphyrin, phthalocyanine and the like, and derivatives thereof.

The ligands having three donor atoms are illustrated in JP-A-H10-145899, JP-A-H10-45901, JP-A-H10-45900, JP-A-2000-226449, JP-A-H10-168180, JP-A-2002-80568, JP-A-2002-80569, JP-A-2002-80586, JP-A-H9-324040, JP-A-H9-324041 or JP-A-H10-45904. Specifically, they are diethylenetriamine, bis(2-pyridylmethyl)amine, bis(2-pyridylethyl)amine, bis(2-imidazolylmethyl)amine, bis(2-oxazolylmethyl)amine, bis(2-thiazolylmethyl)amine, N-(2-pyridylmethylidyne)-N-(2-pyridylmethyl)amine, 2,2':6',2''-terpyridine, 3-(2-pyridylmethylimino)-2-butanoneoxime, tris(2-pyridyl)methane, tris(2-imidazolyl)methane, tris(1-pyrazolyl)methane, tris(1-pyrazolyl)phosphate, tris(1-pyrazolyl)borate, 1,4,7-triazacyclononane and the like, and derivatives thereof.

M represents copper ion, nickel ion, cobalt ion, iron ion, manganese ion, chromium ion or vanadyl ion; and is preferably copper ion, cobalt ion, iron ion, manganese ion or vanadyl ion, more preferably copper ion, cobalt ion or vanadyl ion, and further more preferably copper ion.

When M is copper ion, its valence is 1 or 2; when being nickel ion, its valence is 2 or 3; when being cobalt ion, its valence is 2 or 3; when being iron ion, its valence is from 2 to 5; when being manganese ion, its valence is from 2 to 4; when being chromium ion, its valence is 2 or 3; and when being vanadyl ion, its valence is from 2 or 3.

The complex used in the present invention may have ligand and the like other than the ligand (L) and the atom (M). Said ligand and the like are not particularly limited provided that they do not deactivate catalyst ability; for example, they include a raw material of the complex, a solvent used in a synthesis process and/or an oxidative condensation process.

For the complex used in the present invention, a counter ion (X) may be sometimes necessary to keep electrically neutral. Among counter ions, a conjugate base of Broensted acid is usually used as a counter anion, which, as specific examples, includes fluoride ion, chloride ion, bromide ion, iodide ion, sulphate ion, nitrate ion, carbonate ion, perchlorate ion, tetrafluoroborate ion, hexafluorophosphate ion, methanesulfonic acid ion, trifluoromethanesulfonic acid ion, toluenesulfonic acid ion, acetate ion, trifluoroacetate ion, propionic acid ion, benzoic acid ion, hydroxide ion, oxide ion, methoxide ion, ethoxide ion and the like. The counter anion is preferably chloride ion, bromide ion, iodide ion, sulphate ion, nitrate ion, acetate ion, hydroxide ion or methoxide ion; more preferably chloride ion, bromide ion, sulphate ion or nitrate ion. Moreover, as a counter cation, cations of alkaline metals, alkaline earth metals and the like may be optionally used.

The complex represented by formula (II) used in the present invention, has active parameter Eact. (kcal/mol) defined by the above formula (A) is −21.1 or less and selective parameter Eselect. (kcal/mol) defined by the above formula (B) is −1.7 or less.

When active parameter Eact. (kcal/mol) is more than −21.1, the activity is not sufficient; when selective parameter Eselect. (kcal/mol) is more than −1.7, the selectivity is not sufficient.

The active parameter Eact. (kcal/mol) is preferably −21.1 or less, more preferably −21.2 or less, further more preferably −21.3 or less and particularly preferably −21.4 or less.

The selective parameter Eselect. (kcal/mol) is preferably −1.8 or less, more preferably −2.0 or less, further more preferably −2.2 or less and particularly preferably −2.4 or less.

The complex used in the present invention may be synthesized by a method, for example, of mixing a ligand compound corresponding to L with a metal compound corresponding to M in a suitable solvent. Said complex, although it is possible to use pre-synthesized complex, may be formed in a reaction system.

In the present invention, said complex may be used alone or in combination of two or more thereof.

In the present invention, although said complex may be used in optional amount, the amount of said complex to phenol compound is preferably from 0.001 to 50 percent by mol, more preferably from 0.01 to 10 percent by mol.

The complex used in the present invention preferably includes copper complex represented by the following formula (III),

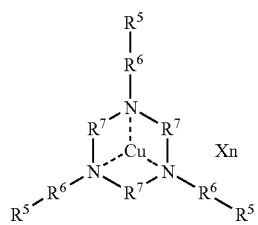

(III)

wherein $R^5$ represents hydrogen atom, cyclic saturated hydrocarbon group, aromatic hydrocarbon group, substituted cyclic saturated hydrocarbon group or substituted aromatic hydrocarbon group, all of $R^5$s may be same or different; $R^6$ represents direct bonding, or divalent hydrocarbon group or substituted hydrocarbon group, all of $R^6$s may be same or different; $R^7$ represents divalent hydrocarbon group or substituted hydrocarbon group, all of $R^7$s may be same or different; Cu, X and n represent the same meaning with those in the above formula (II).

The cyclic saturated hydrocarbon group in $R^5$ represented in the above formula (III) consists of monocyclic saturated hydrocarbon group comprising of one cyclic structure and polycyclic saturated hydrocarbon group comprising of two or more cyclic structures.

Here, monocyclic saturated hydrocarbon group is a group represented by the following formula (IV),

(IV)

wherein $R^8$ represents hydrogen atom or alkyl group, m is an integer of two or more, and all of $R^8$s may be same or different.

The alkyl group of $R^8$ in the above formula (IV) includes methyl group, ethyl group, propyl group, isopropyl group, butyl group, isobutyl group, t-butyl group, pentyl group, hexyl group, nonyl group, dodecyl group and the like. $R^8$ of the above formula (IV) is preferably hydrogen atom or alkyl group having 1 to 20 carbon atoms, more preferably hydrogen atom or alkyl group having 1 to 6 carbon atoms, and further more preferably hydrogen atom or alkyl group having 1 to 4 carbon atoms.

The m of the above formula (IV) is preferably an integer of from 2 to 20, more preferably an integer of from 3 to 11, further more preferably an integer of from 4 to 7.

The polycyclic saturated hydrocarbon group in the cyclic saturated hydrocarbon group of the above formula (IV) includes saturated hydrocarbon groups having the following structures:

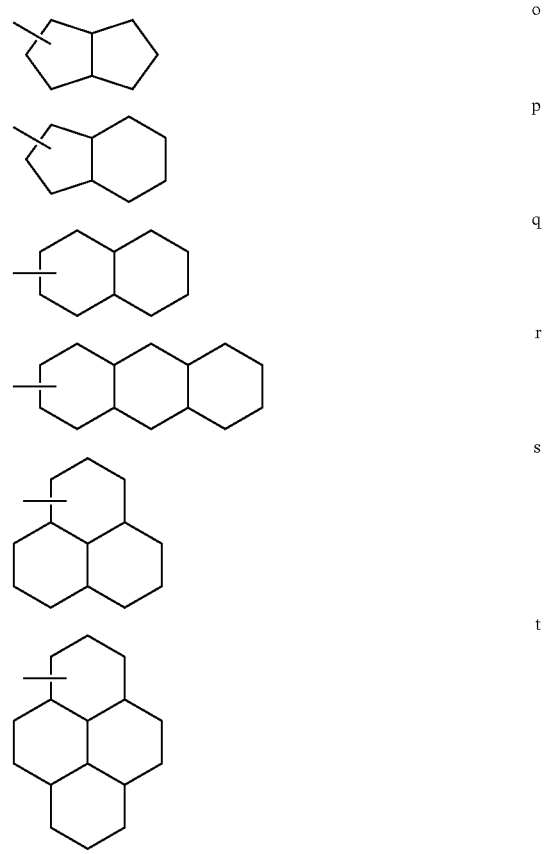

-continued

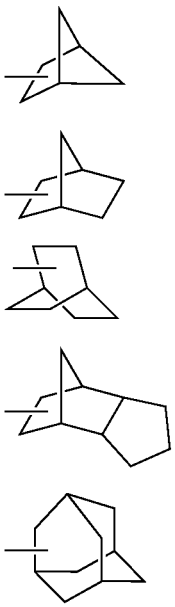

u v w x y

The polycyclic saturated hydrocarbon group in the cyclic saturated hydrocarbon group of the above formula (IV) is preferably a saturated hydrocarbon group having 6 to 50 carbon atoms with the structure of from o to y, and more preferably a saturated hydrocarbon group having 6 to 30 carbon atoms with the structure of from o to y and furthermore preferably a saturated hydrocarbon group having 6 to 20 carbon atoms with the structure of from o to y.

The aromatic hydrocarbon group in $R^5$ of the above formula (III) includes phenyl group, 1-naphthyl group, 2-naphthyl group, 1-anthranyl group, 9-anthranyl group, 2-methylphenyl group, 3-methylphenyl group, 4-methylphenyl group, 4-ethylphenyl group, 4-propylphenyl group, 4-isopropylphenyl group, 4-butylphenyl group, 4-t-butylphenyl group, 4-hexylphenyl group, 4-cyclohexylphenyl group, 4-phenylphenyl group and the like.

The aromatic hydrocarbon group in $R^5$ of the above formula (III) is preferably aromatic hydrocarbon group having 6 to 50 carbon atoms, more preferably aromatic hydrocarbon group having 6 to 30 carbon atoms, and further more preferably aromatic hydrocarbon group having 6 to 20 carbon atoms.

The substituted cyclic saturated hydrocarbon group and substituted aromatic hydrocarbon group in $R^5$ of the above formula (III) include above cyclic saturated hydrocarbon group and aromatic hydrocarbon group substituted with halogen atoms, alkoxy group and the like.

$R^5$ of the above formula (III) is preferably cyclic saturated hydrocarbon group, aromatic hydrocarbon group and substituted aromatic hydrocarbon group, more preferably cyclic saturated hydrocarbon group and aromatic hydrocarbon group, and further more preferably cyclic saturated hydrocarbon group.

The divalent hydrocarbon group in $R^6$ and $R^7$ of the above formula (III) is preferably alkylene group having 1 to 20 carbon atoms, cycloalkylene group having 3 to 20 carbon atoms or arylene group having 6 to 20 carbon atoms. As specific examples, it includes methylene group, ethylene group, 1,2-propylene group, 1,3-propylene group, 2,4-butylene group, 2,4-dimethyl-2,4-butylene group, 1,2-diphenyl-1,2-ethylene group, 1,2-cyclopentylene group, 1,2-cyclohexylene group, 1,2-phenylene group and the like.

The divalent substituted hydrocarbon group in $R^6$ and $R^7$ of the above formula (III) is above divalent hydrocarbon groups substituted with halogen atoms, alkoxy group and the like.

$R^6$ of the above formula (III) is preferably methylene group, ethylene group, halogen-substituted methylene group or halogen-substituted ethylene group. $R^7$ of the above formula (III) is alkylene group having 1 to 8 carbon atoms.

Cu in the above formula (III) represents monovalent or divalent copper ion, and X and n represent the same meaning represented in the above formula (II); and specific examples and preferable examples thereof are also same.

As the complex used in the present invention, it includes more preferably a copper complex represented by the following formula (V),

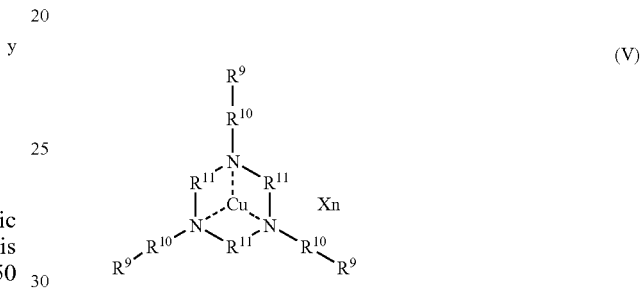

(V)

wherein $R^9$ represents cyclic saturated hydrocarbon group, $R^{10}$ represents methylene group, ethylene group, halogen-substituted methylene group or halogen-substituted ethylene group, $R^{11}$ represents alkylene group having 1 to 8 carbon atoms, plural $R^9$s, $R^{10}$s and $R^{11}$ may be respectively same or different, Cu represents monovalent or divalent copper ion, X represents a counter ion, and n is a number of Xs and is fixed depending on the valences of Cu and X.

The definition, specific examples and preferable examples about the cyclic saturated hydrocarbon group in $R^9$ of the above formula (V) are as same as those of the above formula (III).

$R^{10}$ of the above formula (V) is preferably methylene group, ethylene group, fluorine substituted methylene group and fluorine substituted ethylene group, more preferably methylene group, 1,2-ethylene group, difluoromethylene group, difluoro-1,2-ethylene group and tetrafluoro-1,2-ethylene group, further more preferably methylene group and difluoromethylene group, and particularly preferably methylene group.

$R^{11}$ of the above formula (V) is preferably alkylene group having 2 to 6 carbon atoms, more preferably alkylene group having 2 to 4 carbon atoms, further more preferably 1,2-ethylene group, 1,2-propylene group, 2,3-butylene group and 2,3-dimethyl-2,3-butylene group, and particularly preferably 1,2-ethylene group.

Cu in the above formula (V) represents monovalent or divalent copper ion, and X and n represent the same meaning represented in the above formula (II); and specific examples and preferable examples thereof are also same.

Preferable triamine compound used for the complex of the present invention is represented by the following formula (VI),

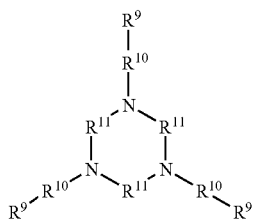

(VI)

wherein $R^9$, $R^{10}$ and $R^{11}$ represent the same meaning represented in the formula (V).

The definition, specific examples and preferable examples about $R^9$, $R^{10}$ and $R^{11}$ of the above formula (VI) are the same with those of the above formula (V).

Triamine compound represented by the formula (VI) of the present invention can be synthesized, for example, by introducing a hydrocarbon group having prescribed number of carbon atoms to each of three nitrogen atoms of a corresponding cyclic triamine (for example, refer J. Chem. Soc. Dalton Trans. 83–90 (1993)).

The copper complex represented by the formula (V) of the present invention, said metal complex can be obtained by reacting triamine compound represented by the formula (VI) with a salt of metal, which is supposed to be a central metal, in a suitable solvent under known method (refer Inorg. Chem. 1379–1381(1980)).

When the copper complex used in the present invention is divalent in its copper valence and has a conjugate base of the acid being stronger than phenol as a counter ion, it is preferable to make one-forth equivalent or more of a base not allowing said copper complex inactive co-existed with said counter ion during polymerization. Example of said base includes hydroxide, oxide and alkoxide of alkaline metals or alkaline earth metals such as sodium hydroxide, potassium hydroxide, calcium oxide, sodium methoxide, sodium ethoxide and the like; amines such as methylamine, ethylamine, propylamine, butylamine, dibutylamine, triethylamine and the like; pyridines such as pyridine, 2-methylpyridine, 2,6-dimethylpyridine, 2,6-diphenylpyridine and the like. It is preferable to make one-forth equivalent or more of alkoxides, amines or pyridines co-existed with a counter ion, more preferable to make one-second equivalent or more of substituted pyridines co-existed with.

On the method for producing phenol condensate of the present invention, an oxidizing agent is oxygen, which may be a mixture with inert gas or be air. The amount of oxygen used is usually used in large excess more than equivalent to phenol compound.

The condensation reaction of the present invention, although it can be carried out without reaction solvent, is generally desired to use solvent. The solvent is not limited provided that it is inactive to phenol compound and liquid at reaction temperature. The exhibition of example of preferred solvent includes aromatic hydrocarbon such as benzene, toluene, xylene and the like; acyclic and cyclic aliphatic hydrocarbon such as heptane, cyclohexane and the like; halogenated hydrocarbon such as chlorobenzene, dichlorobennzene, dichloromethane and the like; nitriles such as acetonitrile, benzonitrile and the like; alcohols such as methanol, ethanol, n-propylalcohol, iso-propylalcohol and the like; ethers such as dioxane, tetrahydrofuran, ethyleneglycoldimethylether and the like; amides such as N,N-dimethylformamide, N-methylpyrolidone and the like; nitro compounds such as nitromethane, nitrobenzene and the like; and water.

Aromatic hydrocarbon, acyclic and cyclic aliphatic hydrocarbon, halogenated hydrocarbon, nitriles, ethers or nitro compounds is more preferable; and aromatic hydrocarbon or halogenated hydrocarbon is further preferable. Those are used alone or a mixture thereof.

When said solvent is used, phenol compound is preferably used in the ratio of concentration of from 0.5 to 50 percent by weight, more preferably of from 1 to 30 percent by weight.

The reaction temperature to carry out condensation reaction of the present invention is not limited provided that the temperature is in the range to keep the reaction solvent in liquid state. When the solvent is not used, the temperature is usually equal or higher than the melting point of phenol compound. Preferable temperature range is from 0 to 200° C., more preferably from 0 to 150° C. and further more preferably from 0 to 100° C. The reaction time, which may vary depending on the reaction conditions such as the reaction temperature and the like, is usually from 1 to 18000 minutes.

EXAMPLES

The present invention is illustrated in more detail with reference to the following Examples, but the scope of the present invention is not limited to the Examples.

Referential Example 1

Calculation of active parameter Eact. (kcal/mol) and selective parameter Eselect. (kcal/mol);

An example is exhibited to calculate each parameter in the case of 4-phenoxyphenol as the phenol compound and of

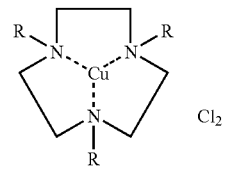

as the copper complex, wherein R is cyclohexylmethyl group, n-butyl group, isopropyl group or cyclohexyl group. Hereinafter, the copper complex of the above structure where R is cyclohexylmethyl group may be abbreviated as Cu(cHexMe3tacn), that of being n-butyl group may be as Cu(nBu3tacn), that of being isopropyl group may be as Cu(iPr3tacn) and that of being cyclohexyl group may be as Cu(cHex3tacn).

For the following structures (a') to (e'), structural optimization was performed by combining WinMOPAC3.0 (FUJITSU LIMITED) with MOPAC transition metal parameter 1, Cu, VO1 (FUJITSU Co.) and by using EF, AM1, MMOK, GNORM=0.10 and CHARGE=1 as key words. When plural optimal structures exist, the one having the lowest heat of formation was selected. Eact.=E(a)–E(c)–E(d) (kcal/mol), and Eselect.={E(a)–E(d)}–{E(b)–E(e)} (kcal/mol) were obtained as shown in Table 1. Here, E(a) to E(e) each respectively represent the value of heat of formation of (a') to (e').

TABLE 1

| Copper Complex | Eact. (kcal/mol) | Eselect. (kcal/mol) |
|---|---|---|
| Cu(cHexMe3tacn) | −21.5 | −2.5 |
| Cu(nBu3tacn) | −28.3 | 1.8 |
| Cu(iPr3tacn) | −21.8 | −1.6 |
| Cu(cHex3tacn) | −21.0 | −2.0 |

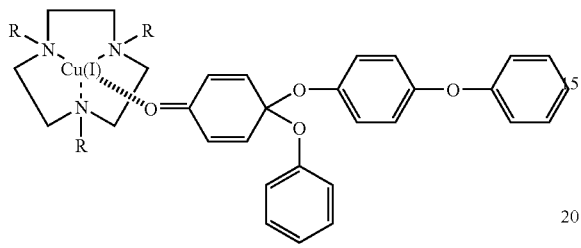

(a')

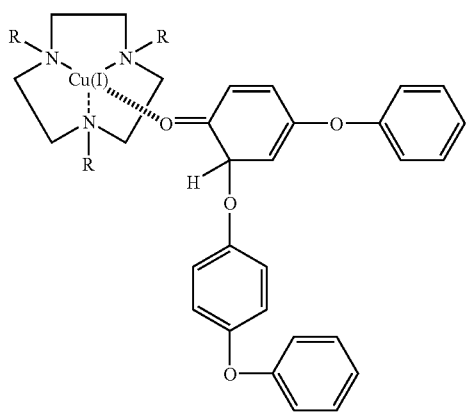

(b')

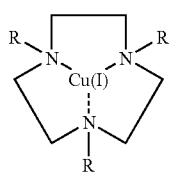

(c')

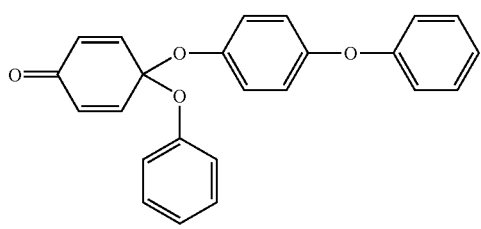

(d')

TABLE 1-continued

| Copper Complex | Eact. (kcal/mol) | Eselect. (kcal/mol) |
|---|---|---|

(e')

Example 1

(i) Synthesis of 1,4,7-tris(cyclohexylmethyl)-1,4,7-triazacyclononane:

1.0 g (7.8 mmol) of 1,4,7-triazacyclononane and 16.7 mL of mesitylene were supplied into a 50 mL two-necked flask equipped with a reflux condenser, and 4.8 g (27 mmol) of cyclohexylmethyl bromide and 2.2 g (39 mmol) of potassium hydroxide were added. The mixture was stirred for 72 hours at 100° C. under argon gas atmosphere. After reaction completed, salt was removed by filtration, and then the filtrate was concentrated and purified by reduced-pressure distillation. (Amount of yield 2.7 g, Yield 83%)

$^1$H-NMR(chloroform-d,ppm):0.75–1.90(m,33H), 2.23(d, 6H), 2.68(s,12H)

$^{13}$C-NMR(chloroform-d,ppm):26.6, 27.3, 32.3, 36.9, 57.0, 67.0 IR(KBr method, cm$^{-1}$): 2919, 2849, 2788, 1448, 1357, 1314, 1263, 1161, 1113, 1033, 997, 965, 892, 843, 792, 728

Elemental analysis/calculated value: C(77.63%), H(12.31%), N(10.06%)/observed value: C(78.02%), H(12.43%), N(9.89%)

(ii) Synthesis of Cu(cHexMe3tacn):

To 0.36 g (0.86 mmol) of 1,4,7-tris(cyclohexylmethyl)-1,4,7-triazacyclononane, 10 mL of dichloromethane/methanol was added to obtain a uniform solution, and then 5 mL of dichloromethane/methanol containing 0.15 g (0.88 mmol) of cupric chloride dehydrate was added. The mixture was stirred for one hour at room temperature. After reaction completed, solvent was removed in vacuum, and then the residue was recrystallized from dichloromethane/methanol. (Amount of yield 0.28 g, Yield 59%)

IR(KBr method, cm$^{-1}$):2929, 2922, 2916, 2849, 1496, 1447, 1106, 1008

Elemental analysis/calculated value: C(58.74%), H(9.31%), N(7.61%)/observed value: C(58.35%), H(9.25%), N(7.58%)

(iii) Oxidative condensation of 4-phenoxyphenol

After replacing the atmosphere in 50 mL two-necked round bottom flask equipped with magnetic stirrer with oxygen, 0.15 mmol of Cu(cHeMe3tacn) was added into the flask, and then 3.0 mmol of 4-phenoxyphenol and 1.5 mmol of 2,6-diphenylpyridine as a base dissolved in 6 g of toluene were added. The mixture was stirred under oxygen atmosphere at 40° C.

At the initial stage of condensation reaction, 15 mg of reaction mixture was taken out and made acidic by a little amount of concentrated HCl aq., and 2 g of methanol was added to prepare a sample for measurement. The sample was analyzed by liquid chromatography (pump: SC8020 system manufactured by TOSOH Co., detector: UV-8020 manufactured by TOSOH Co., detecting wave length: 278 nm, column: ODS-AM304 manufactured by YMC Co., eluent: methanol/water). By plotting the conversion of 4-phenoxyphenol versus time, the reaction speed (%/H) was obtained from the gradient of the plotted line.

From the amounts of four kinds of dimers, that is, 4-[4-(4-phenoxyphenoxy)phenoxy]phenol (p-4), 2-(4-phenoxyphenoxy)-4-phenoxyphenol (o-4), 4,4'-diphenoxy-2,2'-diphenol (o-22) and 4-(4-phenoxyphenoxy)-2,2'-diphenol (oo-13), p/o selectivity defined by "p-4 amount produced/ (o-4 amount produced+oo-22 amount produced+oo13 amount produced)" was obtained.

The value of the reaction speed multiplied by p/o selectivity was defined as speed·selectivity. When the speed·selectivity value is higher, the yield of para-condensate obtained in a given time becomes higher, so the balance between the reaction speed and p/o selectivity was evaluated. The result is shown in Table 2.

Comparative Examples 1–3

Except replacing the catalyst Cu(cHexMe3tacn) used in Example 1 to Cu(nBu3tacn) in case of Comparative Example 1, to Cu(iPr3tacn) in case of Comparative Example 2 and to Cu(cHex3tacn) in case of Comparative Example 3, Comparative Examples were performed with the same manner as performed in Example 1. The results are shown in Table 2.

TABLE 2

| | Catalyst | Reaction Speed (%/h) | p/o Selectivity | Speed · Selectivity |
|---|---|---|---|---|
| Example 1 | Cu(cHexMe3tacn) | 65 | 19 | 1235 |
| Comparative example 1 | Cu(nBu3tacn) | 65 | 9 | 585 |
| Comparative example 2 | Cu(iPr3tacn) | 65 | 13 | 845 |
| Comparative example 3 | Cu(cHex3tacn) | 20 | 19 | 380 |

According to the method for producing phenol condensate of the present invention, in oxidative condensation of a phenol compound not having a substituted group on at least one ortho-position, a condensate coupled at para-position can be produced in an excellent yield.

What is claimed is:

1. A method for producing a phenol condensate comprising oxidative condensation of a phenol compound represented by formula (I), in the presence of a complex represented by formula (II), and oxygen,

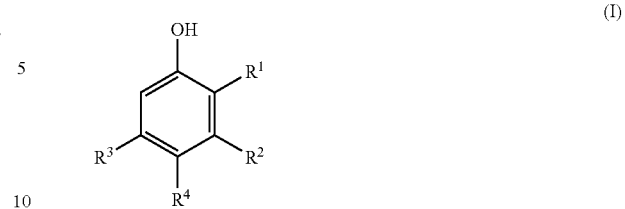

wherein $R^1$, $R^2$ and $R^3$ independently represent hydrogen atom, hydrocarbon group, substituted hydrocarbon group, hydrocarbonoxy group, substituted hydrocarbonoxy group or halogen atoms, $R^1$ and $R^2$ may together form a ring and $R^4$ represents hydrogen atom or phenoxy group, L-M (X)$_n$     (II)

wherein L represents a ligand having 2 to 4 nitrogen atoms as donor atoms, M represents copper ion, nickel ion, cobalt ion, iron ion, manganese ion, chromium ion or vanadyl ion, X represents a counter ion, n is a number of Xs and is fixed depending on the valences of L, M and X;

active parameter Eact. (kcal/mol) defined by the following formula (A) is −21.1 or less and selective parameter Eselect. (kcal/mol) defined by the following formula (B) is −1.7 or less, Eact.=E(a)−E(c)−E(d)     (A)

Eselect.={E(a)−E(d)}−{E(b)−E(e)}     (B)

wherein E(a) to E(e) represent a heat of formation (kcal/mol) when the following structural formulas of from (a) to (e) are respectively structurally optimized with semiempirical molecular orbital method AM1;

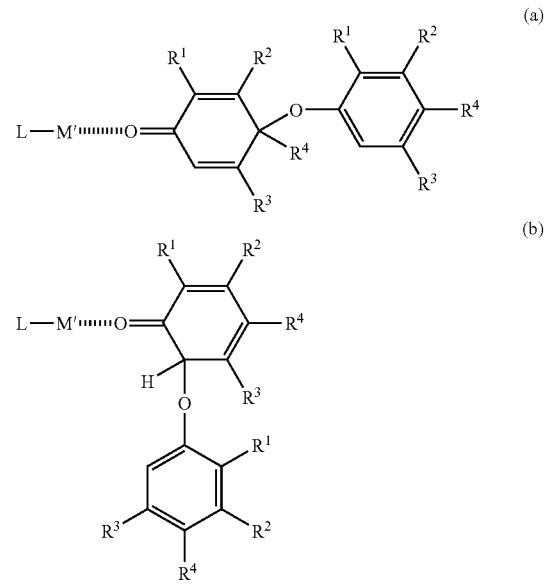

-continued

L—M'

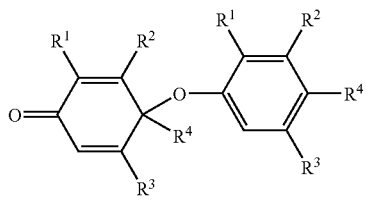

(c)
(d)

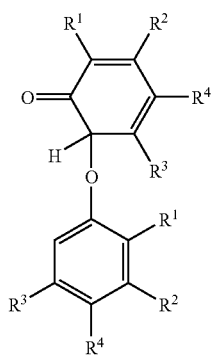

(e)

wherein $R^1$, $R^2$, $R^3$ and $R^4$ represent the same meaning represented in the above formula (I), L, X and n represent the same meaning represented in the above formula (II), and M' respectively represents monovalent copper ion when M is copper ion, divalent nickel ion when M is nickel ion, divalent cobalt ion when M is cobalt ion, divalent iron ion when M is iron ion, divalent manganese ion when M is manganese ion, divalent chromium ion when M is chromium ion and divalent vanadyl ion when M is vanadyl ion.

2. The method for producing a phenol condensate according to claim 1, wherein the complex represented by formula (II) is a copper complex represented by formula (III),

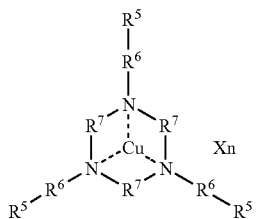

(III)

wherein $R^5$ represents hydrogen atom, cyclic saturated hydrocarbon group, aromatic hydrocarbon group, substituted cyclic saturated hydrocarbon group or substituted aromatic hydrocarbon group, all of $R^5$s may be same or different; $R^6$ represents direct bonding, or divalent hydrocarbon group or substituted hydrocarbon group, all of $R^6$s may be same or different; $R^7$ represents divalent hydrocarbon group or substituted hydrocarbon group, all of $R^7$s may be same or different; Cu represents monovalent or divalent copper ion, and X and n represent the same meaning with those in the above formula (II).

3. The method for producing a phenol condensate according to claim 2, wherein the complex represented by formula (III) is a copper complex represented by formula (V),

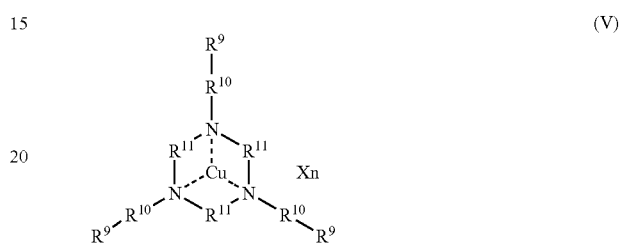

(V)

wherein $R^9$s independently represent cyclic saturated hydrocarbon group, $R^{10}$s independently represent methylene group, ethylene group, halogen-substituted methylene group or halogen-substituted ethylene group, $R^{11}$s independently represent alkylene group having 1 to 8 carbon atoms; Cu represents monovalent or divalent copper ion, X represents a counter ion; and n is a number of Xs and is fixed depending on the valences of Cu and X.

4. A copper complex represented by the above formula (V), as shown in claim 3.

5. A triamine compound represented by the following formula (VI)

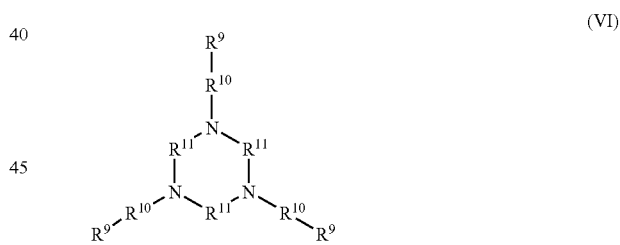

(VI)

wherein $R^9$, $R^{10}$ and $R^{11}$ represent the same meaning with those in the above formula (V), as shown in claim 3.

* * * * *